(12) United States Patent
Liu et al.

(10) Patent No.: US 10,683,260 B2
(45) Date of Patent: Jun. 16, 2020

(54) CRYSTALLINE FORM OF SACUBITRIL SODIUM SALT

(71) Applicant: NORATECH PHARMACEUTICALS, INC., Taipei (TW)

(72) Inventors: Fei Liu, Nanjing (CN); Gang Wu, Nanjing (CN); Weiming Jiang, Nanjing (CN); Cheng-Gang Lin, Nanjing (CN); Xuan Cai, Nanjing (CN); Ping Lin, Nanjing (CN); Yuling Lu, Nanjing (CN); Lixiang Liu, Nanjing (CN)

(73) Assignee: NANJING NORATECH PHARMACEUTICALS CO., LTD., Nanjing (CN)

( * ) Notice: Subject to any disclaimer, the term of this patent is extended or adjusted under 35 U.S.C. 154(b) by 0 days.

(21) Appl. No.: 16/331,088

(22) PCT Filed: Sep. 7, 2016

(86) PCT No.: PCT/CN2016/098288
§ 371 (c)(1),
(2) Date: Mar. 6, 2019

(87) PCT Pub. No.: WO2018/045505
PCT Pub. Date: Mar. 15, 2018

(65) Prior Publication Data
US 2019/0202776 A1    Jul. 4, 2019

Related U.S. Application Data

(60) Provisional application No. PCT/CN2016/098288, filed on Sep. 7, 2016.

(51) Int. Cl.
| | | |
|---|---|---|
| *A61K 31/192* | (2006.01) | |
| *A61K 31/195* | (2006.01) | |
| *A61K 31/216* | (2006.01) | |
| *A61K 31/194* | (2006.01) | |
| *C07C 233/47* | (2006.01) | |
| *A61P 9/12* | (2006.01) | |
| *C07C 231/24* | (2006.01) | |
| *C07C 231/12* | (2006.01) | |
| *A61P 9/04* | (2006.01) | |

(52) U.S. Cl.
CPC .......... *C07C 233/47* (2013.01); *A61K 31/192* (2013.01); *A61K 31/194* (2013.01); *A61K 31/195* (2013.01); *A61K 31/216* (2013.01); *A61P 9/04* (2018.01); *A61P 9/12* (2018.01); *C07C 231/12* (2013.01); *C07C 231/24* (2013.01); *C07B 2200/13* (2013.01); *C07C 2601/16* (2017.05)

(58) Field of Classification Search
None
See application file for complete search history.

(56) References Cited

U.S. PATENT DOCUMENTS 5,217,996 A    6/1993   Ksander

FOREIGN PATENT DOCUMENTS

| CN | 105503638 A | 4/2016 |
| CN | 105693543 A | 6/2016 |
| CN | 105837464 A | 8/2016 |
| WO | WO 2016/074651 A1 | 5/2016 |

OTHER PUBLICATIONS

International Search Report issued in PCT/CN2016/098288 (PCT/ISA/210), dated Jun. 13, 2017.

*Primary Examiner* — Samantha L Shterengarts
(74) *Attorney, Agent, or Firm* — Birch, Stewart, Kolasch & Birch, LLP

(57) ABSTRACT

Provided are new crystalline forms A, B, C, D and E of sacubitril sodium salt and a method for preparation thereof, pharmaceutical compositions thereof, and application thereof in preparing drugs for enkephalinase-related diseases.

19 Claims, 8 Drawing Sheets

CRYSTALLINE FORM OF SACUBITRIL SODIUM SALT

TECHNOLOGY FIELD

The invention relates to the field of pharmaceutical synthesis, particularly to new crystalline forms A, B, C, D and E of sacubitril sodium salts and a method for preparation thereof.

BACKGROUND OF THE INVENTION

Sacubitril, chemical name being 4-{[(2S,4R)-1-([1,1'-biphenyl]-4-yl)-5-ethoxy-4-methyl-5-oxopentan-2-yl]amino}-4-oxobutanoic acid), is an enkephalinase inhibitor. Its structure is as follows:

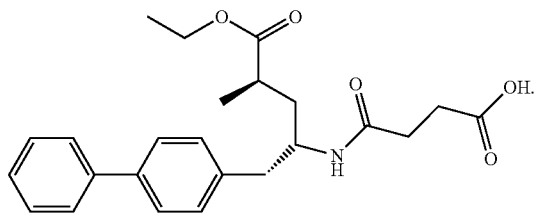

Enkephalinase (NEP) is a metalloproteinase expressed in various tissues and is most abundant in the kidney. It can catalyze the degradation of various endogenous peptides, such as NP, bradykinin, substance P, etc. Therefore, the NEP inhibitor can increase the levels of urinary natriuretic peptide (NP). NP, playing an important role in the body fluid balance, has three subtypes, including type A (ANP), type B (BNP) and type C (CNP). When the blood vessel volume overload causes an increase of atrial pressure, the atrium releases ANP, which is also called atrial natriuretic peptide. Increased left ventricular filling pressure can promote BNP release, and ANP and BNP have effects on the vasodilation and the excretion of sodium as well as diuresis. CNP is mainly expressed in the central nervous system, kidney and vascular endothelial cells, and has an antithrombotic effect. Excessive plasma volume and left ventricular filling pressure can stimulate the release of NP, especially in patients with heart failure. Direct vasodilation of NP reduces ventricular preload, systemic vascular resistance, and arterial pressure, and NP can directly exert vasodilation effect by reducing ventricular preload, systemic vascular resistance, and arterial pressure. In addition, NP can also increase the filtration rate of glomeruli, and promote the excretion of sodium as well as water. NP also reduces the release of renin, lowers plasma angiotensin II levels, and relaxes blood vessels.

Angiotensin II (Ang II) is a potent vasoconstrictor and is the most important active hormone in the renin-angiotensin-aldosterone system (RAAS). It plays a major role in the cardiovascular disease and can exert a direct effect on raising blood pressure. There are at least two subtypes of AngII receptors, including AT1 and AT2. AngII is highly selective for the AT1 receptor and shows 300 times greater affinity than for the AT2 receptor. When AngII binds to the AT1 receptor, it activates the corresponding cellular pathway, thereby exhibiting the main effects of AngII such as vasoconstriction, aldosterone secretion, and renal tubular reabsorption of sodium as well as water. AT1 receptor antagonists can inhibit AngII-mediated vasoconstriction, renal tubular reabsorption of sodium as well as water, regulation of RAAS on baroreceptors, and sympathetic excitation. AT1 receptor antagonists have been widely used in the treatment of hypertension.

The combined administration of sacubitril or its salt with an angiotensin II AT1 receptor antagonist, such as valsartan, can simultaneously inhibit enkephalinase and angiotensin receptor, that is, it can simultaneously act on renin-angiotensin system and promote the circulation of brain natriuretic peptides, thereby acting on the neuroendocrine system of the heart in a variety of ways, blocking receptors that exert harmful effects, and promoting protective mechanisms. LCZ-696 (Entresto), developed by Novartis, is a eutectic composed of sacubitril sodium and valsartan disodium, and used for the treatment of chronic heart failure and/or hypertension with remarkable effects and good safety. At present the drug has been submitted for new drug application in the United States, the European Union and other countries, and has been approved by the FDA, which is the first new drug approved for chronic heart failure in the past 10 years.

Novartis developed sacubitril sodium along with valsartan disodium into the eutectic, LCZ-696. One of the reasons is that LCZ-696 is less hygroscopic than sacubitril sodium, which is more advantageous to production and storage. Although the LCZ-696 eutectic has improved in physical properties, the fixed composition ratio limits the use of combination medication of sacubitril with various ratios of valsartan or its pharmaceutically acceptable salt, or other AT1 receptor antagonists, which is not conducive to clinical adjustment according to different conditions. The free acid of sacubitril is not suitable for the formulation, especially oral solid dosage forms, because of its low melting point and poor water solubility. The amorphous form of the sacubitril sodium salt is highly hygroscopic and difficult to prepare. U.S. Pat. No. 5,217,996 discloses a solid form of sacubitril sodium salt X, which is prepared according to the method thereof, and is found to have a great hygroscopicity. Therefore, it needs to further study the solid form of sacubitril sodium salt in order to obtain the sacubitril sodium salt with simple preparation process and improved physical properties such as hygroscopicity.

It has been demonstrated that it is very difficult to form a sacubitril sodium salt having the desired advantageous properties, and in most cases, the obtained sodium salt forms are poor in stability. This study shows that the crystalline forms of the sacubitril salt in the present invention are particularly advantageous.

SUMMARY OF THE INVENTION

An objective of the present invention is to provide crystalline forms A, B, C, D and E of sacubitril sodium salts.

Another objective of the present invention is to provide a process for the preparation of crystalline forms A, B, C, D and E of sacubitril sodium salts.

The crystalline form A of sacubitril sodium salt of the present invention is characterized in that: by using a Cu-Ka radiation, its X-ray powder diffraction spectrum shows peaks (expressed in degree 2θ) at about 6.0±0.2, 7.0±0.2, 11.8±0.2. 18.2±0.2, 19.7±0.2, and 23.5±0.2; and preferably at about 6.0±0.2, 7.0±0.2, 11.8±0.2, 12.6±0.2, 16.3±0.2, 18.2±0.2, 19.7±0.2, and 23.5±0.2.

In one embodiment, at a heating rate of 10° C./min, the crystalline form A of sacubitril sodium salts has a differential scanning calorimetry thermogram showing an endothermic peak at around 168° C.

In one embodiment, at a heating rate of 10° C./min, the crystalline form A of sacubitril sodium salts has a differential scanning calorimetry thermogram showing an endothermic peak at 166-169° C.

In one embodiment, the crystalline form A of sacubitril sodium salts has an X-ray powder diffraction spectrum substantially the same as that shown in FIG. 1.

In one embodiment, at a heating rate of 10° C./min, the crystalline form A of sacubitril sodium salts has an endothermic curve of differential thermal analysis substantially the same as that shown in FIG. 2.

The differential scanning calorimetry thermogram of the crystalline form A of sacubitril sodium salts shows an endothermic peak at around 166° C. with an enthalpy value of 98.31 J/g. The higher endothermic peak temperature and the enthalpy value indicate a high stability of the lattice of the crystalline form. It should be noted that when maintaining in an open container at a temperature of 25° C. and a relative humidity of 43.5% for 3 hours, the crystalline form has a water content of 1.4%, while the amorphous form under the same condition has a water content as high as 12.8%.

The crystalline form B of sacubitril sodium salts of the present invention is characterized in that: by using a Cu-Ka radiation, its X-ray powder diffraction spectrum shows peaks (expressed in degree 2θ) at about 5.1±0.2, 10.4±0.2, 11.2±0.2, 19.2±0.2, 19.7±0.2, 21.3±0.2, and 21.8±0.2; and preferably at about 5.1±0.2, 8.6±0.2, 10.4±0.2, 11.2±0.2, 12.1±0.2, 19.2±0.2, 19.7±0.2, 21.3±0.2, and 21.8±0.2.

In one embodiment, at a heating rate of 10° C./min, the crystalline form B of sacubitril sodium salts has a differential scanning calorimetry thermogram showing endothermic peaks at around 133° C. and 159° C.

In one embodiment, at a heating rate of 10° C./min, the crystalline form B of sacubitril sodium salts has a differential scanning calorimetry thermogram showing endothermic peaks at 133-134° C. and 149-160° C.

In one embodiment, the crystalline form B of sacubitril sodium salts has an X-ray powder diffraction spectrum substantially the same as that shown in FIG. 3.

In one embodiment, at a heating rate of 10° C./min, the crystalline form B of sacubitril sodium salts has a differential scanning calorimetry thermogram showing an endothermic curve substantially the same as that shown in FIG. 4.

The crystalline form C of sacubitril sodium salts of the present invention is characterized in that: by using a Cu-Ka radiation, its X-ray powder diffraction spectrum shows peaks (expressed in degree 2θ) at about 6.5±0.2, 10.5±0.2, 11.2±0.2, 19.3±0.2, 21.4±0.2, and 22.0±0.2; and preferably at about 6.5±0.2, 10.5±0.2, 11.2±0.2, 12.7±0.2, 14.5±0.2, 16.8±0.2, 19.3±0.2, 21.4±0.2, 22.0±0.2, and 27.2±0.2.

In one embodiment, the crystalline form C of sacubitril sodium salts has a melting point of around 136±5° C.

In one embodiment, the crystalline form C of sacubitril sodium salts has an X-ray powder diffraction spectrum substantially the same as that shown in FIG. 5.

It should be noted when maintaining in an open container at a temperature of 25° C. and a relative humidity of 43.5% for 3 hours, the crystalline form has a water content of 2.4%, while the amorphous form under the same condition has a water content as high as 12.8%.

The crystalline form D of sacubitril sodium salts of the present invention is characterized in that: by using a Cu-Ka radiation, its X-ray powder diffraction spectrum shows peaks (expressed in degree 2θ) at about 5.2±0.2, 8.7±0.2, 10.4±0.2, 12.2±0.2, and 15.7±0.2.

In one embodiment, the crystalline form D of sacubitril sodium salts has a melting point of about 117±5° C.

In one embodiment, the crystalline form D of sacubitril sodium salts has an X-ray powder diffraction spectrum substantially the same as that shown in FIG. 6.

The crystalline form E of sacubitril sodium salts of the present invention is characterized in that: by using a Cu-Ka radiation, its X-ray powder diffraction spectrum shows peaks (expressed in degree 2θ) at about 8.2±0.2, 10.4±0.2, 11.0±0.2, 13.9±0.2, 16.7±0.2, and 21.3±0.2.

In one embodiment, the crystalline form E of sacubitril sodium salts has a melting point of about 130±5° C.

In one embodiment, the crystalline form E of sacubitril sodium salt has an X-ray powder diffraction spectrum substantially the same as that shown in FIG. 7.

The present invention provides a pharmaceutical composition comprising a therapeutically effective amount of the said crystalline forms A, B, C, D or E of sacubitril sodium salts of the present invention in combination with a pharmaceutically acceptable carrier. The pharmaceutical composition can be administered eternally or parentally, and can be administered to a patient in the form of a tablet, a capsule, a solution, a suspension or the like.

The crystalline forms A, B, C, D or E of the sacubitril sodium salts of the present invention, or a pharmaceutical composition comprising the same, can be used, for example, for preventing or treating an enkephalinase-related disease or condition.

The main applications include heart failure, high blood pressure, and cardiomyopathy.

A person skilled in the art is fully enabled to select relevant standard animal experimental models to demonstrate the therapeutic indications and benefits indicated by the context.

In the present invention, the term "the same X-ray powder diffraction spectrum" refers to that the positions of the peaks represented by degrees 2θ are substantially the same, and the relative intensities of the peak positions are substantially the same, wherein the relative intensity refers to a ratio obtained by comparing the intensity of other peaks with the intensity of the strongest peak when the intensity of the peak having the highest intensity among all the diffraction peaks of the X-ray powder diffraction spectrum is set as 100%. It should be noted that the 2θ angle in the X-ray powder diffraction spectrum sometimes has a number of measurement errors due to various factors, and the measured value may usually vary to a degree of ±0.3; preferably ±0.2; and more preferably ±0.1. Therefore, in the present specification, the 2θ angle based on the measured value of a specific sample is understood to comprise these allowable errors. In the present invention, the term "substantially the same as that shown in FIG. 1" refers to at least 50%, or at least 60%, or at least 70%, or at least 80%, or at least 90, or at least 95%, or at least 99% of the peaks appear in the given X-ray powder diffraction spectrum.

It should be explained that the absorption peak in differential scanning calorimetry is an inherent physical property of each crystalline form in the present invention. However, in the actual measurement, in addition to measurement errors, impurities may be mixed in an allowable amount. The possibility of a change in the melting point is also undeniable. Therefore, a person skilled in the art can fully understand to what extent the measured value of the endothermic peak temperature in the present invention can be varied. For example, the conceivable error is, in some cases, about ±5° C.; preferably about ±3° C.; more preferably about ±2° C.; and most preferably about ±1° C.

In the present invention, the term "melting point" refers to the initial melting temperature at which the crystalline form is melted.

The analysis methods used in the present invention are as follows:

1) X-ray powder diffraction

A Bruker D8 advance diffractometer was used. At room temperature, a Cu-Ka fill tube (40 kV, 40 mA) was utilized as an X-ray source with a wide-angle goniometer, and the diffractometer was equipped with a 0.6 mm divergence slit, a 2.5° primary Soller slit, a 2.5° secondary Soller slit, an 8 mm anti-scatter slit, a 0.1 mm detector slit, and a LynxEye detector. In the 2θ continuous scan mode, data was acquired with a scanning step of 0.02° at a scanning speed of 2.4°/min in the range of 3°-40°.

2) Differential scanning calorimetry

Data was acquired using a TA Q200 and a Mettler DSC 1+ before heating from room temperature to degradation temperature at a heating rate of 10° C./min, under the protection of N2 flow at 50 mL/min.

3) Thermogravimetric analyzer

Data was acquired using a TA Q500, and scans were performed from room temperature to until the sample was degradating to less than 30% at a heating rate of 10° C./min, under the protection of N2 flow at 50 mL/min.

DETAILED DESCRIPTION OF THE INVENTION

Figure 1:
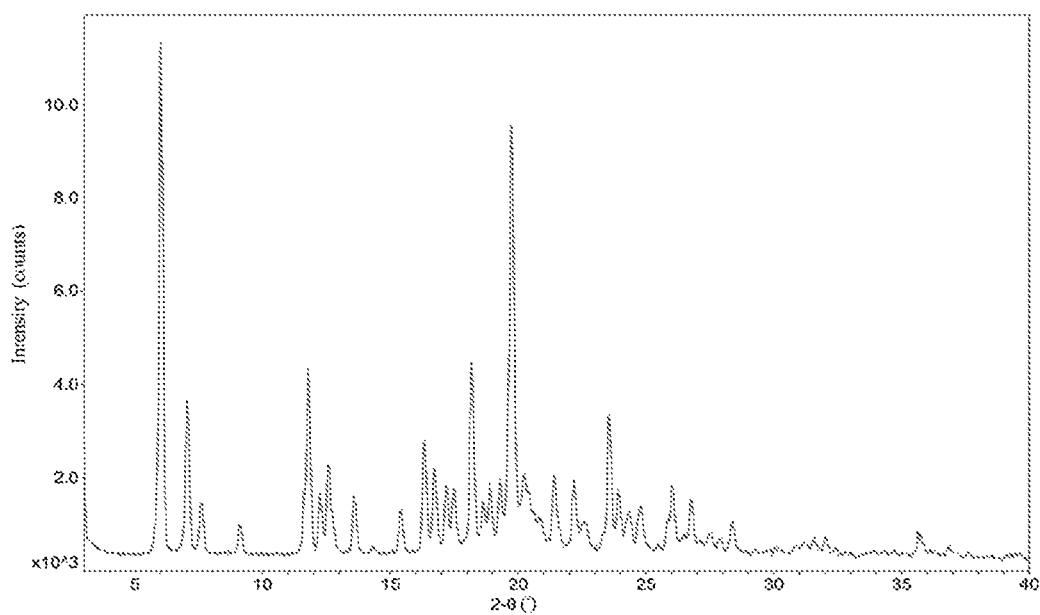
FIG. 1 shows an X-ray powder diffraction (XRD) pattern of a crystalline form A of sacubitril sodium salts.
Figure 2:
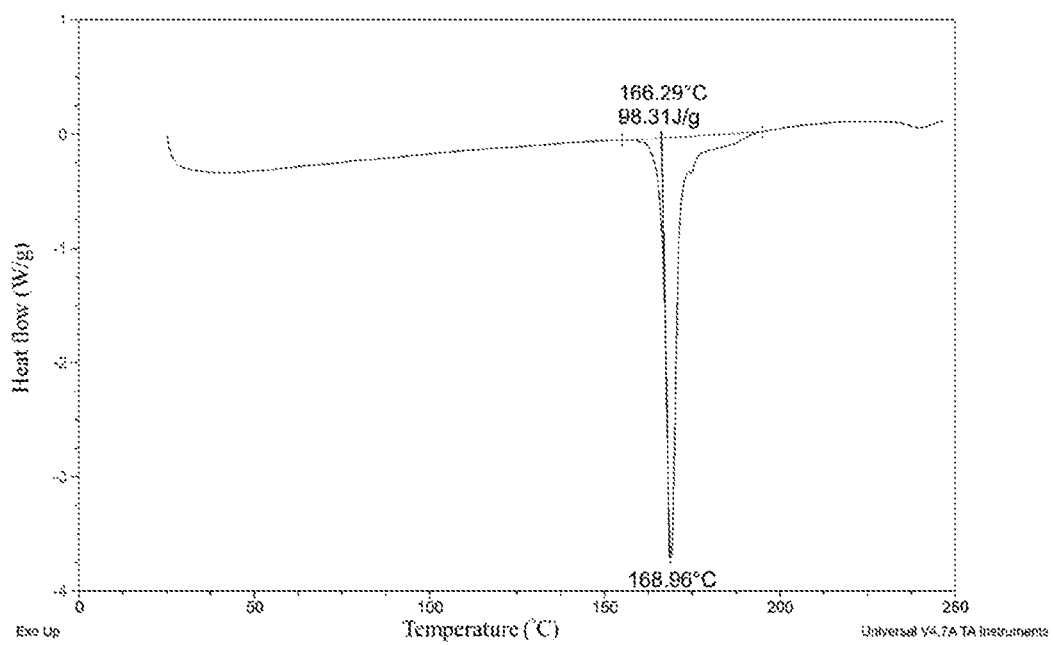
FIG. 2 shows a differential scanning calorimetry (DSC) thermogram of a crystalline form A of sacubitril sodium salts.
Figure 3:
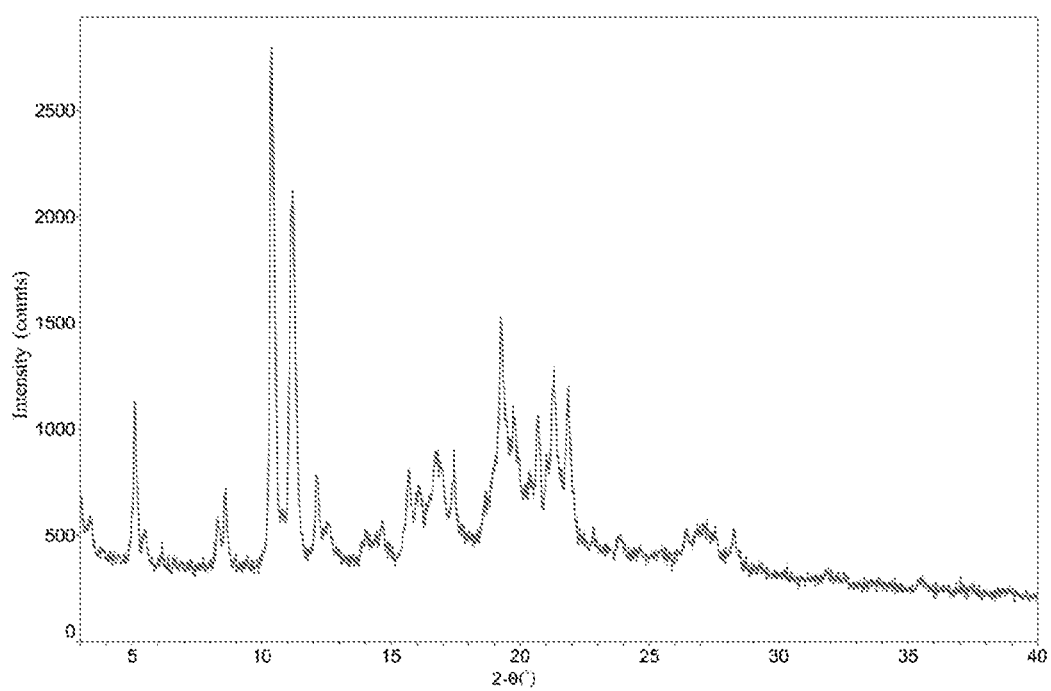
FIG. 3 shows an X-ray powder diffraction (XRD) pattern of a crystalline form B of sacubitril sodium salts.
Figure 4:
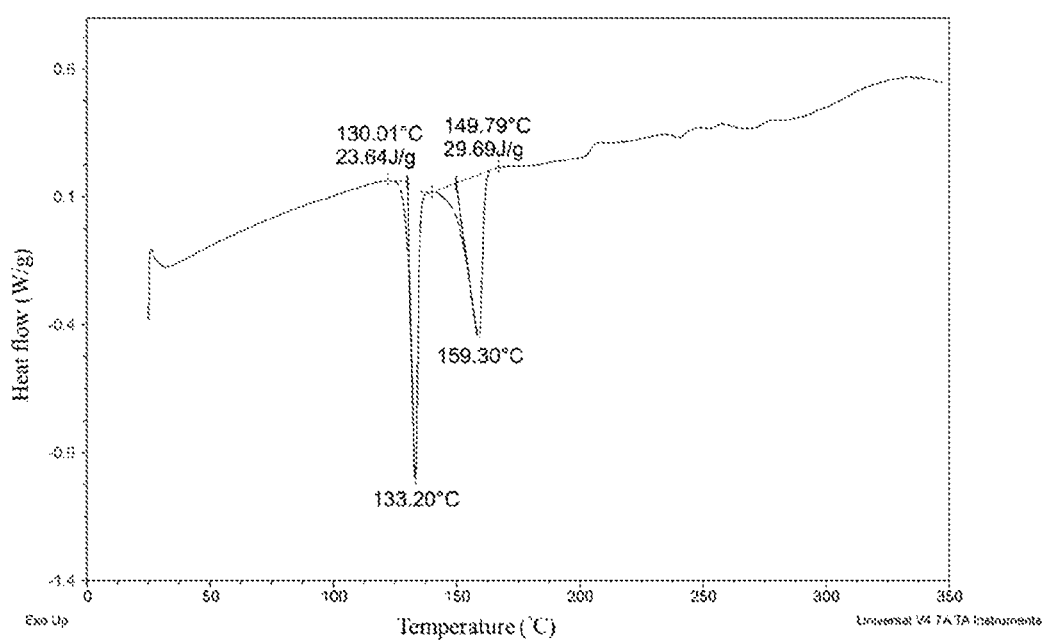
FIG. 4 shows a differential scanning calorimetry (DSC) thermogram of a crystalline form B of sacubitril sodium salts.
Figure 5:
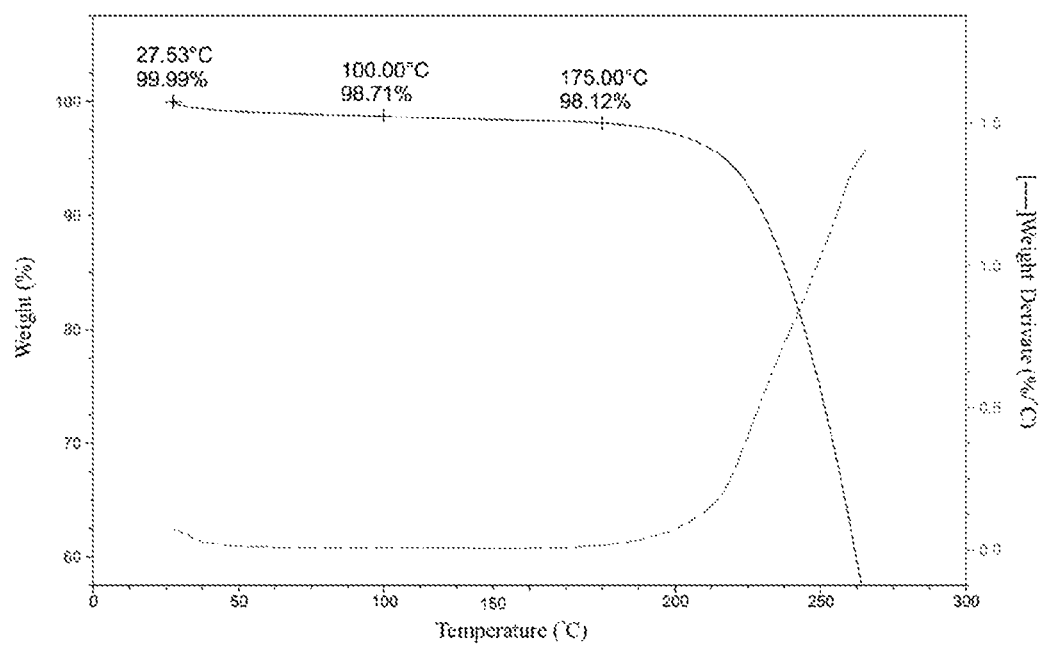
FIG. 5 shows a thermogravimetric analysis (TGA) thermogram of a crystalline form B of sacubitril sodium salts.
Figure 6:
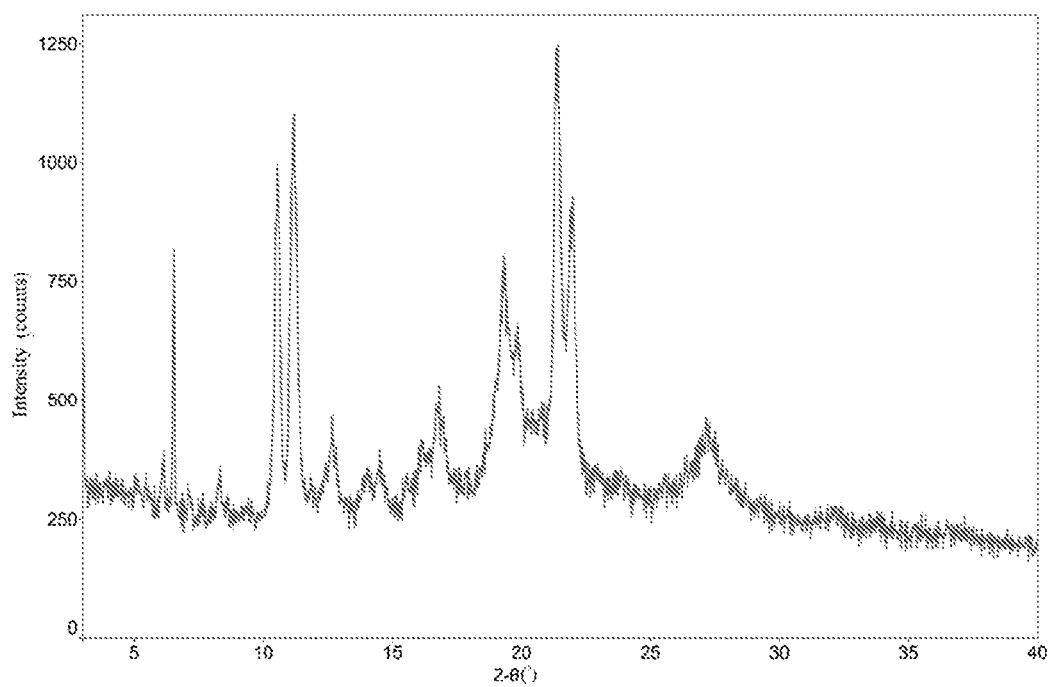
FIG. 6 shows an X-ray powder diffraction (XRD) pattern of a crystalline form C of sacubitril sodium salts.
Figure 7:
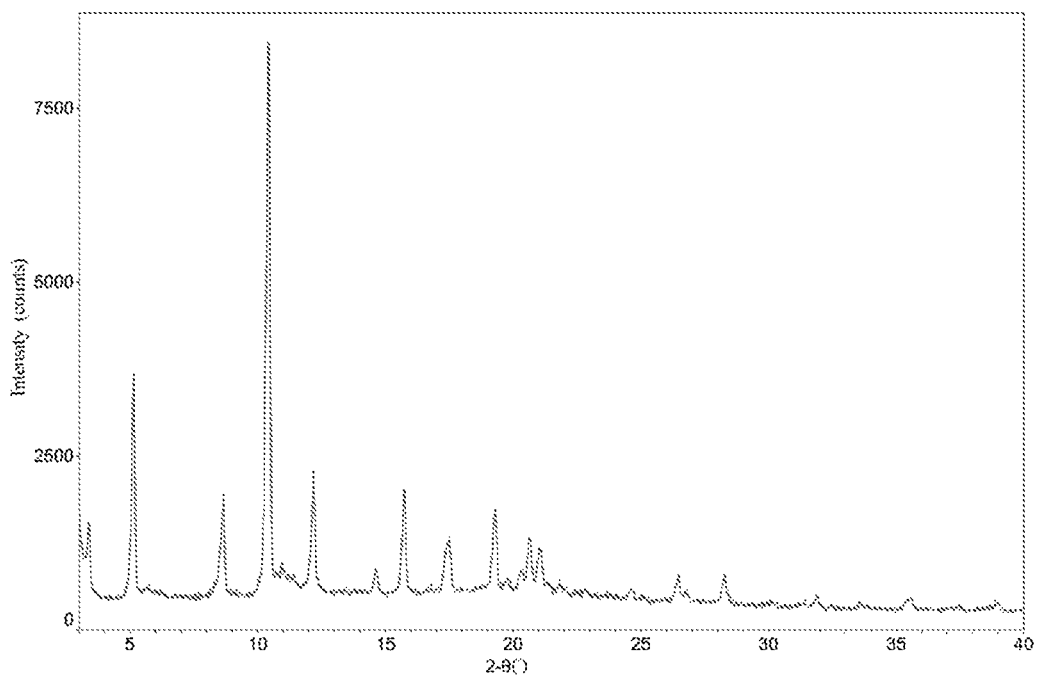
FIG. 7 shows an X-ray powder diffraction (XRD) pattern of a crystalline form D of sacubitril sodium salts.
Figure 8:
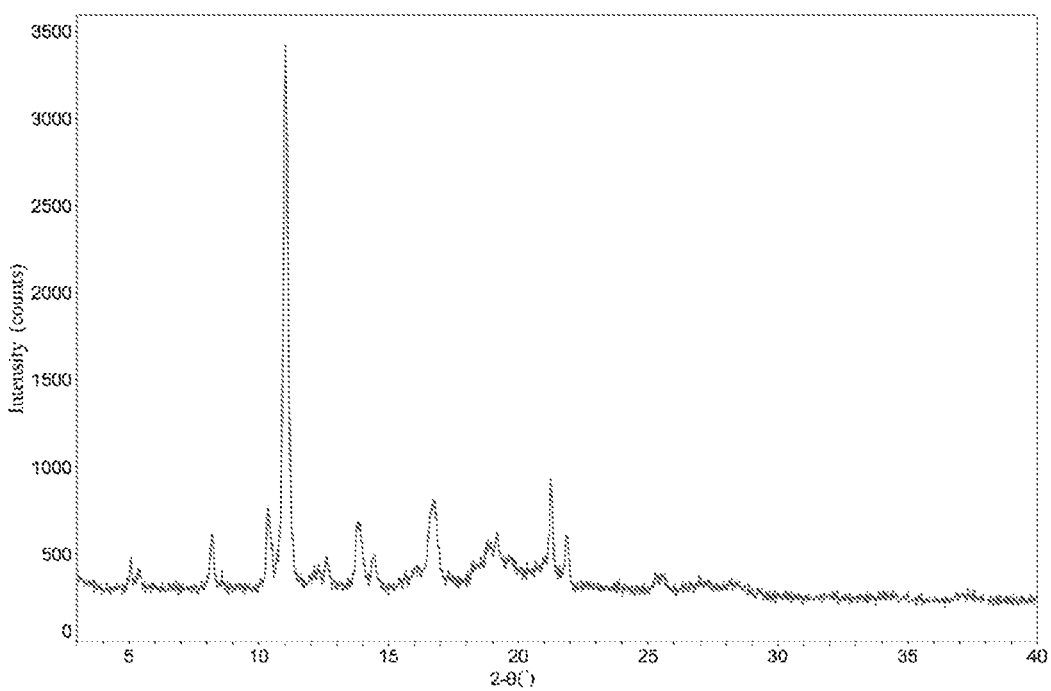
FIG. 8 shows an X-ray powder diffraction (XRD) pattern of a crystalline form E of sacubitril sodium salts.

The above summary of the present invention will be further described with reference to the embodiments of the following examples. However, it should not be understood that the content of the present invention is only limited to the following embodiments, and all the inventions based on the above-mentioned contents of the present invention belong to the scope of the present invention.

COMPARISON EXAMPLE 1

Preparation of Sacubitril Sodium Salt X

The sacubitril sodium salt X was prepared according to the method of Example 1 of U.S. Pat. No. 5,217,996, and the resulting sacubitril sodium salt X had a melting point of 159-160° C.

COMPARISON EXAMPLE 2

Preparation of Amorphous Form of Sacubitril Sodium Salts 1.0 g of sacubitril free acid was suspended in 10 mL of water, and sodium hydroxide solution (97 mg/1 mL) was added dropwise. The mixture was stirred at room temperature for 0.5 h, and the solution was lyophilized to obtain a white powdery solid.

EXAMPLE 1

Preparation of the Crystalline Form A of Sacubitril Sodium Salt 112 mg of sacubitril was dissolved in 2 mL of ethanol, and an ethanol solution containing 10.9 mg of sodium hydroxide per 0.1 mL was added dropwise. The mixture was stirred for 0.5 h, and concentrated under reduced pressure, and the obtained residue was suspended with 300 mL of ethanol/n-heptane (1/19, by volume) and stirred overnight, filtered, and vacuum dried at 40° C. to yield a solid. The solid was added to 10 mL of isopropanol, and after stirring for 72 hours, the supernatant was discarded after centrifugation, and the obtained solid was dried in an oven at 40° C. to yield a white solid, which is a type A sacubitril sodium salt.

This sacubitril sodium salt crystalline form A was subjected to a solid-state characterization by X-ray powder diffraction and differential scanning calorimetry. The solid-state characterization parameters and spectrums are as described herein.

By using a melting point apparatus, the melting of the crystalline form A of sacubitril sodium salts was observed at around 167-168° C.

EXAMPLE 2

Preparation of Crystalline Form B of Sacubitril Sodium Salt 112 mg of sacubitril was dissolved in 2 mL of ethanol, and an ethanol solution containing 9.29 mg of sodium hydroxide per 0.5 mL was added dropwise. The mixture was stirred for 0.5 hour, and concentrated under reduced pressure to obtain a dry solid. 30 mg of the dry solid was dissolved in 0.6 mL of ethanol, and the small glass bottle in which the solution was placed was sealed with a sealing film, and the hole was punched, placed in a glass bottle containing 5 mL of ethyl acetate, and the cap was screwed. After standing at room temperature for 15 days, the small glass bottle was taken out, and the supernatant was discarded after centrifugation to yield a white solid, which is a type B sacubitril sodium salt.

This sacubitril sodium salt crystalline form B was subjected to a solid-state characterization by X-ray powder diffraction and differential scanning calorimetry. The solid-state characterization parameters and spectrums are as described herein.

By using a melting point apparatus, the melting of the crystalline form B of sacubitril sodium salts was observed at around 133-136° C.

EXAMPLE 3

Preparation of Crystalline Form C of Sacubitril Sodium Salt 112 mg of sacubitril was dissolved in 2 mL of ethanol, and an ethanol solution containing 9.29 mg of sodium hydroxide per 0.5 mL was added dropwise. The mixture was stirred for 0.5 hour, and concentrated under reduced pressure to obtain a dry solid. 30 mg of the dry solid was added to 1 mL of isopropanol, and after stirring for 72 hours, the supernatant was discarded after centrifugation, and the obtained solid was dried in an oven at 40° C. to yield a white solid, which is a type C sacubitril sodium salt.

This sacubitril sodium salt crystalline form C was subjected to a solid-state characterization by X-ray powder diffraction. The solid-state characterization parameters and spectrums are as described herein.

By using a melting point apparatus, the melting of the crystalline form C of sacubitril sodium salts was observed at around 136±5° C.

EXAMPLE 4

Preparation of Crystalline Form D of Sacubitril Sodium Salt 112 mg of sacubitril was dissolved in 2 mL of ethanol, and an ethanol solution containing 9.29 mg of sodium hydroxide per 0.5 mL was added dropwise. The mixture was stirred for 0.5 hour, and concentrated under reduced pressure to obtain a dry solid. 30 mg of the dried solid was added to 1 mL of 3-pentanone, and after stirring for 72 hours, the supernatant was discarded after centrifugation, and the obtained solid was dried in an oven at 40° C. to yield a white solid, which is a type D sacubitril sodium salt.

This sacubitril sodium salt crystalline form D was subjected to a solid-state characterization by X-ray powder diffraction. The solid-state characterization parameters and spectrums are as described herein.

By using a melting point apparatus, the melting of the crystalline form D of sacubitril sodium salts was observed at around 117±5° C.

EXAMPLE 5

Preparation of the Crystalline Form E of Sacubitril Sodium Salt 112 mg of sacubitril was dissolved in 2 mL of ethanol, and an ethanol solution containing 9.29 mg of sodium hydroxide per 0.5 mL was added dropwise. The mixture was stirred for 0.5 hour, and concentrated under reduced pressure to obtain a dry solid. 30 mg of the dried solid was added to 1 mL of 2-butanone, dissolved, and ethyl acetate was added dropwise until turbidity appeared. The supernatant was discarded after centrifugation, and the obtained solid was dried in an oven at 40° C. to yield a white solid, which is a type E sacubitril sodium salt.

This sacubitril sodium salt crystalline form E was subjected to a solid-state characterization by X-ray powder diffraction. The solid-state characterization parameters and spectrums are as described herein.

By using a melting point apparatus, the melting of the crystalline form E of sacubitril sodium salts was observed at around 130±5° C.

EXAMPLE 6

Determination of the Hygroscopicity of Each Crystalline Form of Sacubitril Sodium Salt of the Present Invention Analysis method:
1. Take a dry stuffed glass weighing bottle (outer diameter 50 mm, height 15 mm) in the artificial climate chamber (set temperature is 25±1° C., relative humidity is 43.5±2%) and weight it ($m_1$).
2. Take the appropriate amount of the crystalline form in the present invention, and place it in the abovementioned weighing bottle and lay it inside the weighing bottle. The thickness of the test sample is generally about 1 mm. Weight the sample ($m_2$).
3. Uncover the weighing bottle and place it with the bottle cap under constant temperature and humidity (set temperature is 25±1° C., relative humidity is 43.5±2%).
4. Put the cap back on the weighing bottle before weighing, and then weight it ($m_3$). The water absorption percentage for each time point is calculated by the formula=($m_3$−$m_2$)/($m_2$−$m_1$)×100%.

Results:

TABLE 1

| Time  | Crystalline form       | Water absorption, % |
|-------|------------------------|---------------------|
| 1.5 h | amorphous form         | 7.1%                |
| 1.5 h | sacubitril sodium salt X | 8.3%              |
| 1.5 h | A                      | 0.6%                |
| 1.5 h | B                      | 0.5%                |
| 1.5 h | C                      | 1.2%                |
| 1.5 h | D                      | 1.5%                |
| 1.5 h | E                      | 2.4%                |
| 3 h   | amorphous form         | 12.8%               |
| 3 h   | sacubitril sodium salt X | 11.0%             |
| 3 h   | A                      | 1.4%                |
| 3 h   | B                      | 1.0%                |
| 3 h   | C                      | 2.4%                |
| 3 h   | D                      | 3.2%                |
| 3 h   | E                      | 4.3%                |

From the hygroscopicity data shown in Table 1, the crystalline form of the present invention has significantly improved hygroscopicity than the amorphous form as well as the disclosed sacubitril sodium salt X, and is suitable for further development.

The above description merely relates to preferred embodiments in the present invention, and it should be pointed out that, for a person of ordinary skill in the art, some improvements and modifications can also be made under the premise of not departing from the principle of the present invention, and these improvements and modifications should also be considered to be within the scope of protection of the present invention.

What is claimed is:
1. A crystalline form A of sacubitril sodium salt, wherein, the crystalline form has the following properties:
   by using a Cu-Ka radiation, its X-ray powder diffraction spectrum shows peaks at about 6.0±0.2, 7.0±0.2, 11.8±0.2, 18.2±0.2, 19.7±0.2, and 23.5±0.2, expressed in degrees 2θ.
2. The crystalline form A of sacubitril sodium salt according to claim 1, wherein, at a heating rate of 10° C./min, a differential scanning calorimetry thermogram of said crystalline form A of sacubitril sodium salt shows an endothermic peak at around 168° C.

3. The crystalline form A of sacubitril sodium salt according to claim 1, wherein, at a heating rate of 10° C./min, a differential scanning calorimetry thermogram of said crystalline form A of sacubitril sodium salt shows an endothermic peak at around 166-169° C.

4. A crystalline form B of sacubitril sodium salt, wherein, the crystalline form has the following properties:
by using a Cu-Ka radiation, its X-ray powder diffraction spectrum shows peaks at about 5.1±0.2, 10.4±0.2, 11.2±0.2, 19.2±0.2, 19.7±0.2, 21.3±0.2, and 21.8±0.2, expressed in degrees 2θ.

5. The crystalline form B of sacubitril sodium salt according to claim 4, wherein, at a heating rate of 10° C./min, a differential scanning calorimetry thermogram of said crystalline form B of sacubitril sodium salt shows endothermic peaks at around 133° C. and 159° C.

6. The crystalline form B of sacubitril sodium salt according to claim 4, wherein, at a heating rate of 10° C./min, a differential scanning calorimetry thermogram of said crystalline form B of sacubitril sodium salt shows endothermic peaks at 130-134° C. and 149-160° C.

7. A crystalline form C of sacubitril sodium salt, wherein, the crystalline form has the following properties:
by using a Cu-Ka radiation, its X-ray powder diffraction spectrum shows peaks at about 6.5±0.2, 10.5±0.2, 11.2±0.2, 19.3±0.2, 21.4±0.2, 22.0±0.2, expressed in degree 2θ.

8. The crystalline form C of the sacubitril sodium salt according to claim 7, which has a melting point of about 136±5° C.

9. A crystalline form D of sacubitril sodium salt, wherein, the crystalline form has the following properties:
by using a Cu-Ka radiation, its X-ray powder diffraction spectrum shows peaks at about 5.2±0.2, 8.7±0.2, 10.4±0.2, 12.2±0.2, and 15.7±0.2, expressed in degrees 2θ.

10. The crystalline form D of the sacubitril sodium salt according to claim 9, which has a melting point of about 117±5° C.

11. A crystalline form E of sacubitril sodium salt, wherein, the crystalline form has the following properties:
by using a Cu-Ka radiation, its X-ray powder diffraction spectrum shows peaks at about 8.2±0.2, 10.4±0.2, 11.0±0.2, 13.9±0.2, 16.7±0.2, and 21.3±0.2, expressed in degree 2θ.

12. The crystalline form E of the sacubitril sodium salt according to claim 11, which has a melting point of about 130±5° C.

13. A pharmaceutical composition, comprising:
the crystalline form A of sacubitril sodium salt according to claim 1; and
a pharmaceutically acceptable carrier.

14. A pharmaceutical composition, comprising:
the crystalline form B of sacubitril sodium salt according to claim 4; and
a pharmaceutically acceptable carrier.

15. A pharmaceutical composition, comprising:
the crystalline form C of sacubitril sodium salt according to claim 7; and
a pharmaceutically acceptable carrier.

16. A pharmaceutical composition, comprising:
the crystalline form D of sacubitril sodium salt according to claim 9; and
a pharmaceutically acceptable carrier.

17. A pharmaceutical composition, comprising:
the crystalline form E of sacubitril sodium salt according to claim 11; and
a pharmaceutically acceptable carrier.

18. A method for treating enkephalinase-related disease, comprising:
administering the crystalline form A of sacubitril sodium salt according to claim 1 to a subject in need thereof.

19. The method according to claim 18, wherein the disease comprises heart failure, hypertension, and cardiomyopathy.

* * * * *